United States Patent [19]

Saburi et al.

[11] Patent Number: 5,334,758

[45] Date of Patent: Aug. 2, 1994

[54] PROCESS FOR PREPARING OPTICALLY ACTIVE CARBOXYLIC ACID

[75] Inventors: Masahiko Saburi; Masamichi Ohnuki; Yasuzo Uchida, all of Tokyo, Japan

[73] Assignee: Takasago International Corporation, Tokyo, Japan

[21] Appl. No.: 128,759

[22] Filed: Sep. 30, 1993

Related U.S. Application Data

[63] Continuation of Ser. No. 928,174, Aug. 14, 1992, abandoned, which is a continuation of Ser. No. 493,051, Mar. 13, 1990, abandoned.

[30] Foreign Application Priority Data

Jul. 5, 1989 [JP] Japan ................... 1-173835
Dec. 12, 1989 [JP] Japan ................... 1-320472

[51] Int. Cl.$^5$ ............... C07C 55/02; C07C 229/12; C07B 53/00
[52] U.S. Cl. .................. 562/590; 562/433; 562/450; 562/606
[58] Field of Search ............... 562/433, 450, 590, 606

[56] References Cited

U.S. PATENT DOCUMENTS

| | | | |
|---|---|---|---|
| 4,962,230 | 10/1990 | Takaya et al. | 562/433 |
| 5,087,728 | 2/1992 | Nohira et al. | 560/41 |
| 5,107,053 | 4/1992 | Wu | 562/433 |

OTHER PUBLICATIONS

Breger et al., *Chemical Reviews,* vol. 74, No. 5, pp. 567–580 (1974).

*Primary Examiner*—José G. Dees
*Assistant Examiner*—Barbara S. Frazier
*Attorney, Agent, or Firm*—Sughrue, Mion, Zinn, Macpeak & Seas

[57] ABSTRACT

A process for preparing an optically active carboxylic acid is disclosed, comprising asymmetric hydrogenation of an $\alpha,\beta$-unsaturated carboxylic acid using an alcohol as a hydrogen donor in the presence of a metal-optically active phosphine complex. A carboxylic acid having high optical purity can easily be obtained in a high yield without using specific equipment as required in using hydrogen gas as a hydrogen donor.

6 Claims, No Drawings

PROCESS FOR PREPARING OPTICALLY ACTIVE CARBOXYLIC ACID

This is a continuation of application Ser. No. 07/928,174 filed on Aug. 14, 1992 (now abandoned), which is a continuation of prior application Ser. No. 07/493,051 filed Mar. 13, 1990 (now abandoned).

FIELD OF THE INVENTION

This invention relates to a process for preparing an optically active carboxylic acid, and more particularly to a process for preparing an optically active carboxylic acid by asymmetric hydrogenation of an olefin using an alcohol as a hydrogen donor in the presence of a metal complex catalyst.

BACKGROUND OF THE INVENTION

An optically active carboxylic acid is attracting attention as an intermediate for synthesizing useful compounds, such as naturally-occurring physiologically active substances, or a liquid crystal material.

Knowing processes for asymmetric synthesis of an optically active carboxylic acid include (1) a process of using a naturally-occurring optically active substance, (2) a process of utilizing an asymmetric hydrogenation reaction using a microorganism, and (3) a process of asymmetric hydrogenation using a specific catalyst.

Among them, included in a process for obtaining an optically active carboxylic acid through asymmetric synthesis from an α,β-unsaturated carboxylic acid is the process disclosed in JP-A-63-239245 (the term "JP-A" as used herein means an "unexamined published Japanese patent application").

The conventional techniques of asymmetric hydrogenation generally employ hydrogen gas as a source of hydrogen and hence require a pressure-resistant reactor for hydrogenation, e.g., an autoclave, and attachment equipment, such as a bomb or a pressure tank for feeding hydrogen gas. Thus, these processes involve difficulty in handling the equipment.

SUMMARY OF THE INVENTION

In the light of the above-described situation, the inventors have conducted extensive investigations and, as a result, it has now been found that an optically active carboxylic acid of high optical purity can be obtained easily by asymmetric hydrogenation of an α,β-unsaturated carboxylic acid using an alcohol as a hydrogen source in the presence of a relatively cheap metal-optically active phosphine complex.

This invention provides a process for preparing an optically active carboxylic acid comprising asymmetric hydrogenation of an α,β-unsaturated carboxylic acid in the presence of a metal-optically active phosphine complex using an alcohol as a hydrogen donor.

DETAILED DESCRIPTION OF THE INVENTION

The α,β-unsaturated carboxylic acid which is a substrate of asymmetric hydrogenation according to the present invention preferably includes a compound represented by formula (I):

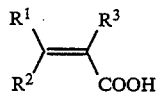

(I)

wherein $R^1$ and $R^2$ each represents a hydrogen atom, an alkyl group, an aryl group, a carboxyl group, or a carboxyalkyl group; and $R^3$ represents a hydrogen atom, an alkyl group, an aryl group, a carboxyalkyl group, or a protected amino group; provided that $R^1$, $R^2$, and $R^3$ are so combined that the α-carbon atom and/or β-carbon atom becomes an asymmetric carbon atom on hydrogenation of the α,β-double bond. In order that one or both of the α-carbon atom and β-carbon atom of the resulting carboxylic acid is/are an asymmetric carbon atom(s), when $R^3$ is a hydrogen atom, for instance, $R^1$ and $R^2$ should be groups which are different from each other, other than a hydrogen atom and a carboxymethyl group; and when $R^3$ is a methyl group, for instance, either one of $R^1$ and $R^2$ and should be a hydrogen atom, with the other being a group other than a hydrogen atom.

From the standpoint of reaction efficiency, it is preferable that any one of $R^1$, $R^2$, and $R^3$ be a hydrogen atom.

The alkyl group as represented by $R^1$, $R^2$ or $R^3$ preferably includes an alkyl group having from 1 to 6 carbon atoms; the aryl group as represented by $R^1$, $R^2$ or $R^3$ preferably includes a phenyl group, a naphthyl group, and a tolyl group; and the carboxyalkyl group as represented by $R^1$, $R^2$, or $R^3$ preferably includes a carboxymethyl group.

The protected amino group as represented by $R^3$ includes an N-acyl group such as an N-acetyl group and an N-propionyl group; and an N-carbonylalkoxy group such as an N-carbonylethoxy group and an N-carbonyl-t-butoxy group.

Specific examples of suitable α,β-unsaturated carboxylic acids are itaconic acid, citraconic acid, tiglic acid, atropic acid, benzylidenesuccinic acid, α-benzylacrylic acid, α-methylcinnamic acid, acetamidocinnamic acid, and angelic acid.

The hydrogen donor which can be used in the present invention includes a primary alcohol and a secondary and preferably those represented by formula (IV):

$$R^5R^6CHOH \quad (IV)$$

wherein $R^5$ and $R^6$ each represents a hydrogen atom, an alkyl group, a cycloalkyl group, or an aryl group.

Of the alcohols of formula (IV), those having at least 2 carbon atoms are preferred. Examples of suitable compounds having 2 or more carbon atoms are ethanol, propanol, butanol, isopropyl alcohol, isobutanol, pentanol, cyclohexanol, cyclopentanol, benzyl alcohol, p-methoxybenzyl alcohol, and 2,4-dimethoxybenzyl alcohol.

The alcohol is preferably used in large excess with respect to the substrate (usually from 20 to 130 molar times the substrate) in order to ensure a high reaction rate.

The metal-optically active phosphine complex which can be used as a catalyst in the present invention includes complexes formed between a metal element, e.g., ruthenium, rhodium, and palladium, and an optically active phosphine compound, and preferably a ruthenium-optically active phosphine complex represented by formulae (II) or (III):

RuH(R⁴-BINAP)₂X  (II)

Ru₂Cl₄(R⁴-BINAP)₂(Y)  (III)

wherein R⁴-BINAP represents a tertiary phosphine represented by formula:

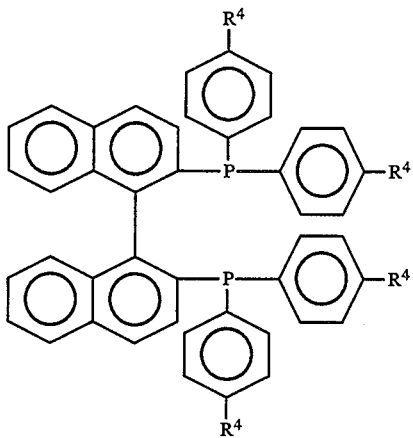

R⁴ represents a hydrogen atom or a methyl group; X represents a hydrogen atom, a chlorine atom, ClO₄, BF₄, or PF₆; and Y represents a tertiary amine.

Specific examples of the tertiary amine as represented by Y include triethylamine, tributylamine, and pyridine.

The ruthenium-optically active phosphine complex represented by formula (II) can be prepared by the process described in M. Saburi, et al., *Chemistry Letters*, pp. 2055–2058 (1988), and the ruthenium-optically active phosphine complex represented by formula (III) can be prepared by the process described in T. Ikariya, et al., *J. Chem. Soc., Chem. Commun.*, pp. 922–924 (1985).

Specific examples of suitable ruthenium-optically active phosphine complex which can be used in the present invention are shown below:

---
[RuH((+)-BINAP)₂]PF₆
[wherein BINAP represents 2,2′-bis(diphenylphosphino)-1,1′-binaphthyl]
[RuH((−)-BINAP)₂]PF₆
RuH₂((−)-BINAP)₂
RuHC((+)-BINAP)₂
RuHC((−)-Tol-BINAP)₂
[wherein Tol-BINAP represents 2,2′-bis(di-p-tolylphosphino)-1,1′-binaphthyl]
[RuH((+)-BINAP)₂]BF₆
Ru₂Cl₄((+)-BINAP)₂NEt₃
[wherein Et represents an ethyl group]
Ru₂Cl₄((−)-BINAP)₂NEt₃
Ru₂Cl₄((−)-Tol-BINAP)]₂NEt₃
Ru₂Cl₄((+)-BINAP)₂NBu₃
[wherein Bu represents a butyl group]
---

In carrying out the process of the present invention, an α,β-unsaturated carboxylic acid and a large excess of an alcohol are dissolved in a solvent, e.g., tetrahydrofuran, dichloromethane, and toluene, and a metal-optically active phosphine complex is added to the solution in an amount of from 1/50 to 1/1000 mole per mole of the carboxylic acid to perform asymmetric hydrogenation in a nitrogen atmosphere at a temperature of from 50° to 100° C. for a period of from 5 to 20 hours. After the reaction, the solvent is removed by distillation, and the residue is neutralized. The catalyst is then removed by extraction with chloroform, dichloromethane, etc. The extract is again acidified with a mineral acid, followed by extraction with diethyl ether, chloroform, dichloromethane, etc. to thereby recover the desired optically active carboxylic acid.

The present invention is now illustrated in greater detail by way of the following Examples, but it should be understood that the present invention is not construed as being limited thereto.

EXAMPLE 1

Asymmetric Hydrogenation of Itaconic Acid

In a 20 ml-volume Schlenk's tube were charged 65.0 mg (0.5 mmole) of itaconic acid and 14.91 mg (0.01 mmole) of [RuH((−)-BINAP)₂]PF₆, and 2.5 ml of tetrahydrofuran (THF) and 2.5 ml (32.7 mmole) of isopropyl alcohol were added thereto. The mixture was heated at reflux in an oil bath at 85° C. for 24 hours. The solvent was removed by distillation under reduced pressure. The residue was dissolved in 20 ml of a 1M sodium hydroxide aqueous solution and washed three times with each 10 ml portions of chloroform. The aqueous layer was adjusted to a pH of 1 with concentrated hydrochloric acid and then extracted three times with each 10 ml portions of diethyl ether. The combined ether layer was dried over magnesium sulfate, and the solvent was removed to give 47 to 60 mg of methylsuccinic acid as a white solid.

The enantiomer excess (hereinafter referred to as "e.e.") of the resulting methylsuccinic acid was determined as follows. A part (1.32 mg, 0.1 mmole) of the crude product was dissolved in 2 ml of THF and 2 ml of acetonitrile, and 45.4 mg (0.22 mmole) of N,N′-dicyclohexylcarbodiimide, 2.4 mg (0.02 mmole) of 4-dimethylaminopyridine, and 0.01 ml (0.11 mmole) of aniline were added to the solution, followed by stirring at room temperature overnight. The solvent was removed from the reaction mixture by distillation under reduced pressure. The residue was dissolved in chloroform, washed three times with a 5M hydrochloric acid aqueous solution and then once with a saturated sodium hydrogencarbonate aqueous solution in a successive manner, and dried over magnesium sulfate. The solvent was removed, and the crude dianilide was purified by silica gel column chromatography using diethyl ether as an eluent. The purified dianilide was subjected to high performance liquid chromatography (HPLC) using a chromatograph equipped with CHIRALCEL-OD ® (manufactured by Daicel Chemical Industries, Ltd.) (eluent: isopropyl alcohol/hexane=10/90 by volume; detection: UV 254 nm; flow rate: 1 ml/min) to determine the e.e.

The yield (% based on the converted amount) was determined from the ¹H-NMR spectrum (400 MHz).

The reaction results thus obtained are shown in Table 1 below.

EXAMPLES 2 TO 4

Asymmetric hydrogenation of itaconic acid was carried out in the same manner as in Example 1, except for replacing the catalyst used in Example 1 with each of the ruthenium-phosphine complexes shown in Table 1 below. The reaction results are shown in Table 1.

TABLE 1

| Example No. | Catalyst* | Conversion (%) | Yield (% based on converted amount) | e.e. (%) | Configuration |
|---|---|---|---|---|---|
| 1 | A | 100 | 100 | 97 | R |
| 2 | B | 100 | 100 | 95 | R |
| 3 | C | 100 | 100 | 92 | R |
| 4 | D | 100 | 94 | 93 | R |

Note:
A: [RuH((−)-BINAP)$_2$]PF$_6$
B: RuH$_2$((−)-BINAP)$_2$
C: RuHCl((−)-BINAP)$_2$
D: Ru$_2$Cl$_4$((−)-BINAP)$_2$NEt$_3$

EXAMPLES 5 TO 11

Asymmetric hydrogenation of itaconic acid was carried out in the same manner as in Example 1, except for using each of the alcohols shown in Table 2 below. The reaction results are shown in Table 2 together with the results of Examples 1 and 2.

TABLE 2

| Example No. | Catalyst* | Alcohol | Conversion (%) | e.e. (%) | Configuration |
|---|---|---|---|---|---|
| 5 | A | ethanol | 100 | 91 | R |
| 1 | A | isopropyl alcohol | 100 | 97 | R |
| 6 | A | benzyl alcohol | 100 | 95 | R |
| 7 | A | benzyl alcohol** | 37 | 94 | R |
| 8 | A | methanol | 30 | 41 | R |
| 9 | B | ethanol | 100 | 92 | R |
| 2 | B | isopropyl alcohol | 100 | 95 | R |
| 10 | B | benzyl alcohol | 100 | 95 | R |
| 11 | B | methanol | 15 | 38 | R |

Note:
*A: [RuH((−)-BINAP)$_2$]PF$_6$
B: RuH$_2$((−)-BINAP)$_2$
**benzyl alcohol/itaconic acid = 2.7/1 (by mole)

As is apparent from the results of Example 7 shown above, when the alcohol was used in an amount about three times the molar quantity of the substrate (itaconic acid), although the e.e. underwent no substantial change, the conversion was greatly reduced. This indicates that the reaction rate decreases unless the alcohol exists in large excess.

Further, in Examples 8 and 11 where methanol was used as an alcohol, both e.e. and conversion were reduced.

EXAMPLES 12 TO 16 AND COMPARATIVE EXAMPLE 1

Asymmetric hydrogenation of an α,β-unsaturated carboxylic acid was carried out in the same manner as in Example 1, except for using citraconic acid as a substrate, each of the ruthenium-phosphine complexes shown in Table 3 below as a catalyst, and each of the alcohols shown in Table 3 as a hydrogen donor.

For comparison, asymmetric hydrogenation of citraconic acid was carried out using RuHCl(−)-BINAP)$_2$ as a catalyst and hydrogen gas as a hydrogen donor according to the process described in M. Saburi, et al., Tetrahedron Lett., Vol. 28 p. 1905 (1987).

The reaction results are shown in Table 3.

TABLE 3

| Example No. | Catalyst* | Alcohol | Conversion (%) | Yield (% based on converted amount) | e.e. | Configuration |
|---|---|---|---|---|---|---|
| 12 | A | ethanol | 100 | 81 | 48 | R |
| 13 | B | ethanol | 100 | 83 | 39 | R |
| 14 | C | ethanol | 100 | 84 | 11 | R |
| 15 | A | isopropyl alcohol | 100 | 80 | 36 | R |
| 16 | A | benzyl alcohol | 100 | 58 | 35 | R |
| Comparative Example 1 | C | H$_2$ | 39 | — | 34 | S |

Note:
*A: [RuH((−)-BINAP)$_2$]PF$_6$
B: RuH$_2$((−)-BINAP)$_2$
C: RuHCl((−)-BINAP)$_2$

EXAMPLE 17

Asymmetric Hydrogenation of Tiglic Acid

To a mixture of 102.7 mg (1.03 mmole) of tiglic acid and 27.9 mg (0.0207 mmole) of RuH$_2$((−)-BINAP)$_2$ were added 2.5 ml of THF and 2.5 ml (24.2 mmole) of benzyl alcohol under a nitrogen atmosphere, and the mixture was heated at reflux in an oil bath at 85° C. for 24 hours. After completion of the reaction, the reaction mixture was worked-up in the same manner as in Example 1 (i.e., alkali extraction and acid extraction) to give a mixture of methyl butyrate and unreacted tiglic acid as a colorless oily substance. The yield was determined from the $^1$H-NMR spectrum (400 MHz) of the oily substance. The e.e. was determined by HPLC of an anilide of the crude product. As a result, the conversion and e.e. were found to be 44% and 37%, respectively.

EXAMPLES 18 TO 25

Asymmetric Hydrogenation of α-Acetamido-(Z)-Cinnamic Acid

Asymmetric hydrogenation of an α,β-unsaturated carboxylic acid was carried out in the same manner as in Example 1, except for using α-acetamido-(Z)-cinnamic acid as a substrate, each of the ruthenium-phosphine complexes shown in Table 4 below as a catalyst, and each of the alcohols shown in Table 4 as a hydrogen donor. The reaction results are shown in Table 4.

The e.e. of the resulting N-acetylphenylalanine was determined as follows. Diazomethane was generated from 107.1 mg (0.5 mmole) of p-toluenesulfonyl-N-methyl-N-nitrosoamide, potassium hydroxide, and carbitol. Separately, 20.5 mg (0.1 mmole) of the above prepared crude product was dissolved in 2 ml of ethanol, and diazomethane was fed thereto together with diethyl ether vapors in a nitrogen atmosphere to convert the product into a methyl ester. After completion of the esterification, the solvent was removed by distillation, and the resulting N-acetylphenylalanine methyl ester was subjected to HPLC using a chromatograph equipped with CHIRALCEL-OD ® to determine the e.e.

TABLE 4

| Example No. | Catalyst* | Alcohol | Reaction Temp. (°C.) | Conversion (%) | e.e. (%) | Configuration |
|---|---|---|---|---|---|---|
| 18 | A | ethanol | 80 | 100 | 67 | S |
| 19 | A | isopropyl alcohol | 80 | 100 | 67 | S |
| 20 | B | benzyl alcohol | 80 | 75 | 73 | S |
| 21 | C | isopropyl alcohol | 80 | 100 | 37 | R |
| 22 | D | isopropyl alcohol | 80 | 22 | 72 | S |
| 23 | A | ethanol | 50 | 84 | 86 | S |
| 24 | A | isopropyl alcohol | 50 | 57 | 96 | S |
| 25 | B | ethanol | 50 | 18 | 83 | S |

Note:
*A: [RuH((−)-BINAP)$_2$]PF$_6$
B: RuH$_2$((−)-BINAP)$_2$
C: RuHCl((+)-*BINAP*)$_2$
D: Ru$_2$Cl$_4$((+)-BINAP)$_2$NEt$_3$

EXAMPLES 26 TO 35

Preparation of α-Methylbutyric Acid by Asymmetric Hydrogenation of Angelic Acid

Asymmetric hydrogenation of an α,β-unsaturated carboxylic acid was carried out in the same manner as in Example 1, except for using angelic acid as a substrate, each of the ruthenium-phosphine complexes shown in Table 5 below as a catalyst, and each of the alcohols shown in Table 5 as a hydrogen donor. The reaction results are shown in Table 5.

In Table 5, the e.e. was determined in the same manner as in Examples 1 to 17.

TABLE 5

| Example No. | Catalyst* | Alcohol | Reaction Temp. (°C.) | Conversion (%) | Yield α-Methylbutyric Acid (%) | Yield Tiglic Acid (%) | e.e. (%) | Configuration |
|---|---|---|---|---|---|---|---|---|
| 26 | A | ethanol | 80 | 100 | 97 | 3 | 57 | R |
| 27 | A | isopropyl alcohol | 80 | 36 | 32 | 4 | 54 | R |
| 28 | A | benzyl alcohol | 80 | 97 | 88 | 9 | 50 | R |
| 29 | B | ethanol | 80 | 20 | 13 | 7 | 42 | R |
| 30 | B | benzyl alcohol | 80 | 82 | 31 | 51 | 35 | R |
| 31 | C | ethanol | 80 | 46 | 42 | 4 | 53 | R |
| 32 | C | isopropyl alcohol | 80 | 90 | 75 | 15 | 46 | R |
| 33 | D | ethanol | 80 | 10 | 8 | 2 | 29 | R |
| 34 | E | ethanol | 80 | 100 | 91 | 9 | 52 | R |
| 35 | A | ethanol | 50 | 57 | 55 | 2 | 58 | R |

Note:
*A: [RuH((−)-BINAP)$_2$]PF$_6$
B: RuH$_2$((−)-BINAP)$_2$
C: RuHCl((−)-*BINAP*)$_2$
D: Ru$_2$Cl$_4$((−)-BINAP)$_2$NEt$_3$
E: [RuH((−)-*p-tolyl-BINAP*)$_2$]PF$_6$ As described above, the present invention makes it possible to carry out asymmetric hydrogenation of an α,β-unsaturated carboxylic acid in an extremely higher optical yield as compared with the conventional processes.

While the invention has been described in detail and with reference to specific embodiments thereof, it will be apparent to one skilled in the art that various changes modifications can be made therein without departing from the spirit and scope thereof.

What is claimed is:

1. A process for preparing an optically active carboxylic acid comprising asymmetric hydrogenation of an α,β-unsaturated carboxylic acid using an alcohol as a hydrogen donor in the presence of a metal-optically active phosphine complex, wherein said alcohol is used in a molar ratio of from 2 to 130 times that of the α,β-unsaturated carboxylic acid, and wherein said asymmetric hydrogenation is performed in a nitrogen atmosphere.

2. A process as claimed in claim 1, wherein said α,β-unsaturated carboxylic acid is represented by formula (I):

wherein R$^1$ and R$^2$ each represents a hydrogen atom, an alkyl group, an aryl group, a carboxyl group, or a carboxyalkyl group; and R$^3$ represents a hydrogen atom, an alkyl group, an aryl group, a carboxyalkyl group, or a protected amino group; provided that R$^1$, R$^2$, and R$^3$ are so combined that the α-carbon atom and/or β-carbon atom becomes an asymmetric carbon atom on hydrogenation of the α,β-double bond.

3. A process as claimed in claim 1, wherein said metal-optically active phosphine complex is a ruthenium-optically active phosphine complex represented by formula (II):

wherein R$^4$-BINAP represents a tertiary phosphine represented by formula:

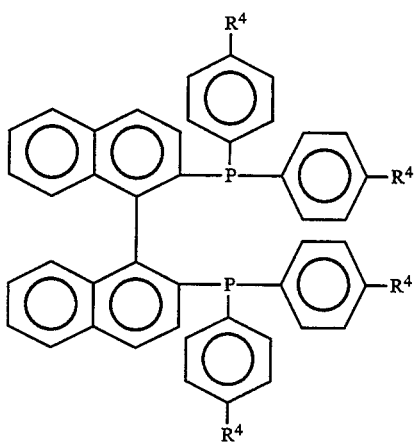

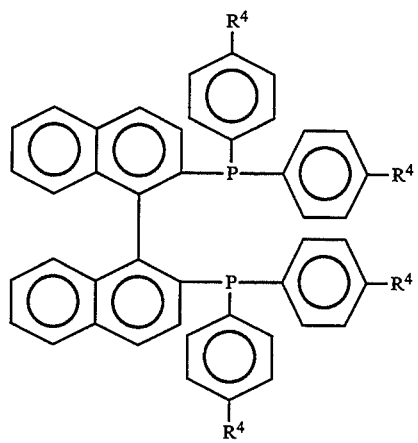

$R^4$ represents a hydrogen atom or a methyl group; and X represents a hydrogen atom, a chlorine atom, $ClO_4$, $BF_4$, or $PF_6$.

4. A process as claimed in claim 1, wherein said metal-optically active phosphine complex is a ruthenium-optically active phosphine complex represented by formula (III):

$$Ru_2Cl_4(R^4\text{-BINAP})_2(Y) \tag{III}$$

wherein $R^4$-BINAP represents a tertiary phosphine represented by formula:

$R^4$ represents a hydrogen atom or a methyl group; and Y represents a tertiary amine.

5. A process as claimed in claim 1, wherein said alcohol is represented by formula (IV):

$$R^5R^6CHOH \tag{IV}$$

wherein $R^5$ and $R^6$ each represents a hydrogen atom, an alkyl group, a cycloalkyl group, or an aryl group.

6. A process as claimed in claim 5, wherein said alcohol contains at least two carbon atoms.

* * * * *